United States Patent [19]

Jin et al.

[11] Patent Number: 5,267,559

[45] Date of Patent: Dec. 7, 1993

[54] ATRIAL DEFIBRILLATOR AND METHOD FOR PROVIDING ATRIAL SENSING

[75] Inventors: Yixuan Jin, Mercer Island; Kenneth R. Infinger, Redmond, both of Wash.

[73] Assignee: InControl, Inc., Redmond, Wash.

[21] Appl. No.: 965,166

[22] Filed: Oct. 23, 1992

[51] Int. Cl.$^5$ ............................................. A61N 1/39
[52] U.S. Cl. .................................................. 128/419 D
[58] Field of Search ........................ 128/419 D, 419 PG

[56] References Cited

U.S. PATENT DOCUMENTS

| | | | |
|---|---|---|---|
| 3,738,370 | 6/1973 | Charms | 128/419 D |
| 3,952,750 | 4/1976 | Mirowski et al. | 128/419 D |
| 4,114,627 | 9/1978 | Lewyn et al. | 128/419 PG |
| 4,343,311 | 8/1982 | Markowitz | 128/419 PG |
| 4,390,020 | 6/1983 | Herpers | 128/419 PG |
| 4,407,287 | 10/1983 | Herpers | 128/419 PG |
| 5,086,772 | 2/1992 | Larnard et al. | 128/419 D |
| 5,117,824 | 6/1992 | Keimel et al. | 128/419 PG |
| 5,165,403 | 11/1992 | Mehra | 128/419 D |

Primary Examiner—William E. Kamm
Assistant Examiner—Kennedy J. Schaetzle
Attorney, Agent, or Firm—Foley & Lardner

[57] ABSTRACT

An implantable atrial defibrillator applies cardioverting electrical energy to the atria of a human heart in need of cardioversion. The atrial defibrillator includes a first detector for sensing atrial activity of the heart, an atrial fibrillation detector responsive to the first detector for determining when the atria of the heart are in need of cardioversion and a second detector for detecting ventricular activations of the heart. The atrial defibrillator further includes a cardioverter for applying cardioverting electrical energy to the atria of the heart when the atria of the heart are in need of cardioversion and is responsive to the second detector for applying the cardioverting electrical energy to the atria of the heart in predetermined time relation to a detected ventricular activation. The detection of atrial activity of the heart is interrupted when a ventricular activation of the heart is detected by the second detector.

9 Claims, 2 Drawing Sheets

ATRIAL DEFIBRILLATOR AND METHOD FOR PROVIDING ATRIAL SENSING

BACKGROUND OF THE INVENTION

The present invention generally relates to an atrial defibrillator and method for applying cardioverting electrical energy to the atria of a human heart in need of cardioversion. The present invention is more particularly directed to a fully automatic implantable atrial defibrillator which exhibits improved atrial sensing by interrupting the detection of atrial activity of the heart when a ventricular activation (R wave) of the heart is detected.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Improved atrial defibrillators and lead systems which exhibit both automatic operation and improved operation are fully described in copending U.S. application Ser. No. 07/685,130, filed Apr. 12, 1991, in the names of John M. Adams and Clifton A. Alferness for IMPROVED ATRIAL DEFIBRILLATOR AND METHOD and U.S. application Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. As disclosed in the aforementioned referenced applications, synchronizing the delivery of the defibrillating or cardioverting electrical energy to the atria with a ventricular electrical activation (R wave) of the heart has been considered important to avoid inducing ventricular fibrillation. Ventricular fibrillation is a fatal arrhythmia which can be caused by electrical energy being delivered to the heart at the wrong time in the cardiac cycle, such as during the T wave of the cycle. The atrial defibrillators of the aforementioned referenced applications exhibit improved safety from inducing ventricular fibrillation by sensing ventricular activations of the heart in a manner which avoids detecting noise as ventricular electrical activations for generating reliable synchronization signals. Hence, these implantable atrial defibrillators, by providing such noise immunity in R wave detection assure reliable synchronization.

It is equally as important for an atrial defibrillator to reliably sense atrial activity. It is the atrial activity of the heart sensed by an automatic implantable atrial defibrillator which is utilized by the defibrillator to determine if atrial fibrillation is present and hence if the atria of the heart are in need of cardioversion. The atrial defibrillator of the aforementioned referenced applications include atrial electrodes for both applying cardioverting electrical energy to the atria and for enabling the sensing of atrial activity of the heart. One electrode is placed in the right atrium and another electrode is fed into the coronary sinus to a position near the left ventricle adjacent the left atrium. This electrode placement confines substantially all of the cardioverting electrical energy to the atria of the heart. The foregoing electrode placement also permits bipolar sensing of the activity of the atria.

In accordance with the referenced copending applications, the atrial defibrillators disclosed therein continuously detect ventricular activations of the heart. The ventricular activations are recorded and analyzed and when the ventricular activation rate indicates the potential of atrial fibrillation, the sensing of atrial activity is enabled along with an atrial fibrillation detector. The sensed atrial activity is digitized into digital samples which are recorded and then analyzed by the atrial fibrillation detector. The atrial fibrillation detector is implemented by a microprocessor which processes the recorded digital samples in accordance with a stored algorithm. If it is determined that the atria are in fibrillation and thus in need of cardioversion, the microprocessor causes cardioverting electrical energy to be stored in a storage capacitor which, at an appropriate time, is discharged into the atrial electrodes for cardioverting the atria.

In processing the atrial activity digital samples to determine if the atria are in fibrillation, it is most desirable for the digital samples processed by the atrial fibrillation detector to be representative of only the activity of the atria. However, since the ventricular activations are the most prominent electrical signals produced by the heart, the ventricular activations may also be sensed by the atrial electrodes along with the atrial activity. This becomes more likely if the atrial electrodes are widely spaced apart and/or close to at least one of the ventricles of the heart.

The atrial defibrillator and method of the present invention provides improved atrial activity sensing by interrupting the detection of atrial activity of the heart when ventricular activations (R waves) of the heart are detected. This assures that the atrial fibrillation detector will process only digital samples of atrial activity when detecting for atrial fibrillation. As disclosed herein in connection with the preferred embodiment in accordance with the present invention, the interruption in atrial activity detection may be accomplished by disabling the atrial sense amplifier coupled to the atrial electrodes during ventricular activations and/or by the microprocessor precluding the recording of atrial activity during ventricular activations. With either or both implementations, it will be assured that the atrial fibrillation determination is based solely upon atrial activity of the heart.

SUMMARY OF THE INVENTION

The present invention therefore provides an implantable atrial defibrillator for applying cardioverting electrical energy to the atria of a human heart in need of cardioversion. The atrial defibrillator includes first detecting means adapted for sensing activity of the heart in at least on of the atria of the heart, atrial fibrillation detecting means responsive to the first detecting means for determining when the atria of the heart are in need of cardioversion, and second detecting means for detecting ventricular activations of the heart. The atrial defibrillator further includes cardioverting means for applying cardioverting electrical energy to the atria of the heart when the atria of the heart are in need of cardioversion and being responsive to the second detecting means for applying the cardioverting electrical energy to the atria of the heart in predetermined time relation to a detected ventricular activation, and means for causing the atrial fibrillation detecting means to be responsive to only atrial activity sensed by said first detecting means for determining when the atria are in need of cardioversion.

The present invention also provides an implantable atrial defibrillator for applying cardioverting electrical energy to the atria of a human heart in need of cardioversion. The atrial defibrillator includes first detecting means for sensing atrial activity of the heart, atrial fibrillation detecting means responsive to the first detecting means for determining when the atria of the heart are in need of cardioversion, and second detecting means for detecting ventricular activations of the heart. The atrial defibrillator further includes cardioverting means for applying cardioverting electrical energy to the atria of the heart when the atria of the heart are in need of cardioversion and being responsive to the second detecting means for applying the cardioverting electrical energy to the atria of the heart in predetermined time relation to a detected ventricular activation, and means for interrupting the sensing of atrial activity of the heart responsive to the detection of ventricular activations of the heart by the second detecting means.

The present invention further provides a method of applying cardioverting electrical energy to the atria of a human heart in need of cardioversion. The method includes the steps of sensing activity of the heart in at least one of the atria of the heart, and detecting ventricular activations of the heart. The method further includes the steps of determining from only the atrial activity of the heart sensed in the at least one of the atria when the atria are in need of cardioversion, and applying cardioverting electrical energy to the atria of the heart when the atria are in need of cardioversion and in predetermined timed relation to a detected ventricular activation of the heart.

The present invention still further provides a method of applying cardioverting electrical energy to the atria of a human heart in need of cardioversion. The method includes the steps of sensing atrial activity of the heart, detecting ventricular activations of the heart, and interrupting the sensing of atrial activity of the heart when ventricular activations of the heart are detected. The method further includes the steps of determining from the sensed atrial activity of the heart when the atria are in need of cardioversion, and applying cardioverting electrical energy to the atria of the heart when the atria are in need of cardioversion and in predetermined timed relation to a detected ventricular activation of the heart.

BRIEF DESCRIPTION OF THE DRAWINGS

The features of the present invention which are believed to be novel ar set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENTS

Figure 1:
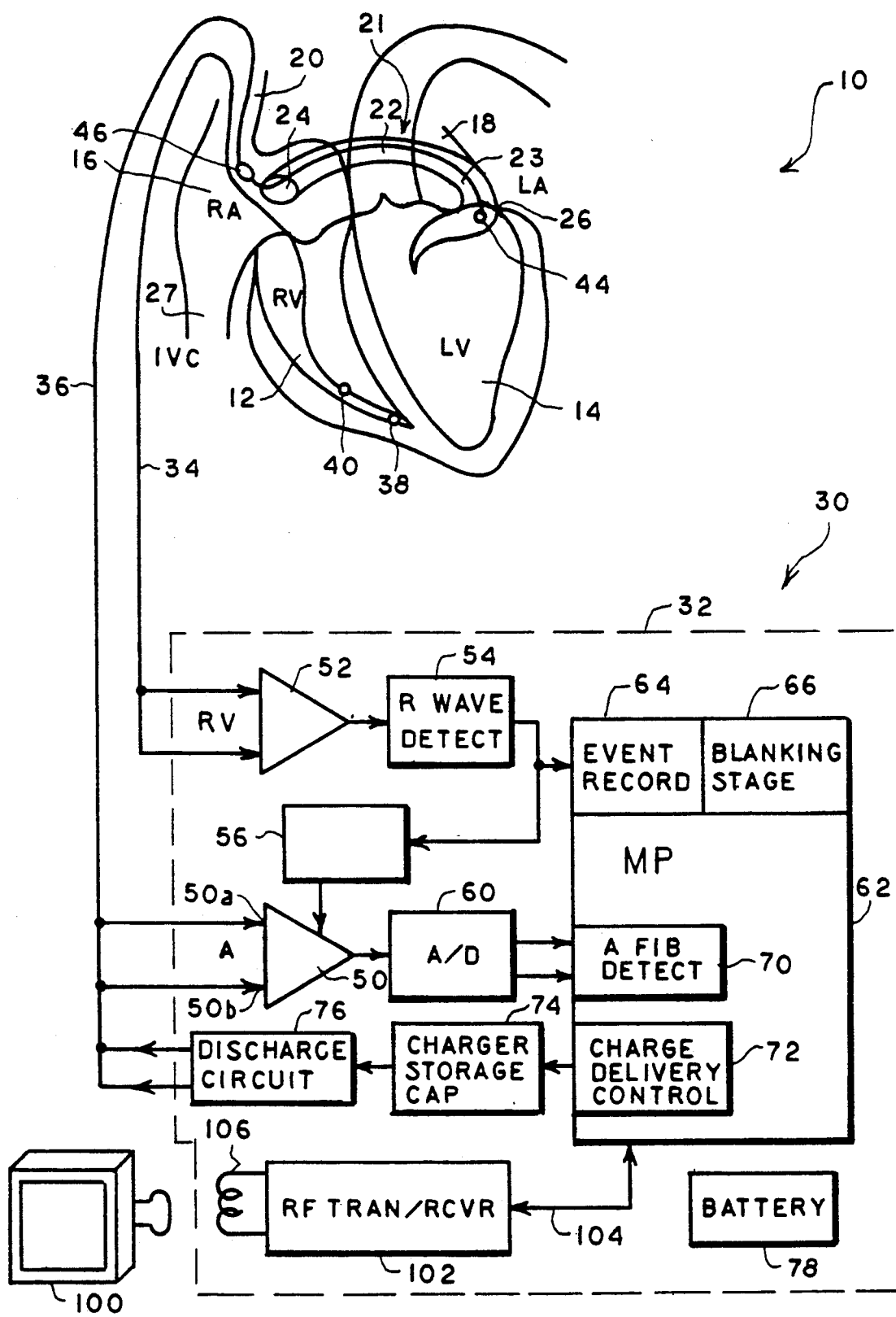
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Prior to referring to FIG. 1, a general description of a typical or normal cardiac cycle may be helpful in understanding the operation and various aspects of the present invention. The beginning of a cardiac cycle is initiated by a P wave which is normally a small positive wave. The P wave is the depolarization of the atria of the heart. Following the P wave there is a cardiac cycle portion which is substantially constant in amplitude. This substantially constant portion will have a time duration on the order of, for example, 120 milliseconds.

The QRS complex of the cardiac cycle the normally occurs after the substantially constant portion. The dominating feature of the QRS complex is the R wave which is a rapid positive or negative deflection. The R wave generally has an amplitude greater than any other wave of the cardiac cycle and will have a spiked shape of relatively short duration with a sharp rise, a peak amplitude, and a sharp decline. The R wave is the depolarization of the ventricles and hence, as used herein, the term "ventricle activations" denotes R waves of the heart cardiac cycle.

Following the QRS complex, the cardiac cycle is completed with the T wave which is separated from the QRS complex by about 250 milliseconds. The T wave is relatively long in duration of, for example, on the order of 150 milliseconds. During the T wave, the heart is most vulnerable to induced ventricular fibrillation should the heart be cardioverted during this period. The next cardiac cycle begins with the next P wave. The duration of a cardiac cycle may be on the order of 800 milliseconds.

As will be appreciated by those skilled in the art, the characteristics of a cardiac cycle of a heart experiencing atrial fibrillation will be distinctly different than described above for a normal cardiac cycle. During atrial fibrillation, there generally are no discernable P waves because the atria are in an unstable or fibrillating condition. As a result, the atrial activity of the heart is represented by low amplitude electrical signals. Ventricular activations (R waves) are still present and remain the most dominate wave represented by comparatively high amplitude electrical signals.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 3 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is fed through the superior vena cava 20, into the right atrium 16, and then into the right ventricle 12.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, a second sense amplifier 52, and an R wave detector 54. The first sense amplifier 50 together with the first electrode 44 and second electrode 46 of the lead 36 to which it is coupled form a first detecting means or atrial channel for sensing atrial activity of the heart. The second sense amplifier 52 and the R wave detector 54 together with electrodes 38 and 40 of the lead 34 to which sense amplifier 52 is coupled form a second detecting means or ventricular channel for detecting ventricular activations of the right ventricle 12.

The output of sense amplifier 52 is coupled to the R wave detector 54. The R wave detector 54 is of the type well known in the art which provides an output pulse upon the occurrence of an R wave being sensed during a cardiac cycle of the heart. The output of sense amplifier 50 is coupled to an analog to digital converter 60 which converts the analog signal representative of the activity of the heart being sensed by electrodes 44 and 46 and amplifier 50 to digital samples.

As will be noted, and in accordance with one aspect of the present invention, a disable circuit 56 is coupled between R wave detector 54 and sense amplifier 50. The sense amplifier 50 is preferably of the type having a differential input including inputs 50a and 50b which are arranged to be short circuited together responsive to a control signal from disable circuit 56. The disable circuit 56 is of the type which generates the control signal responsive to the output pulse of R wave detector 54 when a ventricular activation is detected. The control signal generated by the disabling circuit 56 preferably has a duration equal to or slightly longer than a ventricular activation. This assures that the differential input including inputs 50a and 50b are short circuited for the entire duration of each detected R wave. As a result, the sense amplifier 50 will be disabled from sensing activity of the heart when an electrical activation is detected.

Alternatively, or in combination with the above the sense amplifier 50 may be of the type having a selectable high and relatively low gain responsive to the control signal provided by disable circuit 56. More specifically, when the sense amplifier 50 senses heart activity in the atria, it will have the high gain. However, when a ventricular activation is detected, the control signal provided by disable circuit 56 causes the relatively low gain of sense amplifier 50 to be selected. In accordance with this preferred embodiment, the high gain of sense amplifier 50 may be on the order of 1000 and the relatively low gain on the order of 100. Because the electrical signals other than ventricular activation sensed in the atria are of low amplitude, the selectable gains interrupt the sensing of heart activity by sense amplifier 50 when ventricular activations are detected and the relatively low gain is selected.

The enclosure 32 of the atrial defibrillator 30 further includes a microprocessor 62. The microprocessor 62 is preferably implemented in a manner as disclosed in the aforementioned copending U.S. application Ser. Nos. 07/685,130 and 07/856,514 and further as described hereinafter with respect to FIG. 2. The implementation of the microprocessor 62 in accordance with this embodiment of the present invention results in a plurality of functional stages. The stages include an event recorder 64, a blanking stage 66, an atrial arrythmia detector in the form of an atrial fibrillation detector 70, and a charge delivery and energy control stage 72.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data in the memory at the addresses defined by multiple-bit addresses conveyed over the address bus and coveys the data to the memory 92 over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, the microprocessor 62 receives programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in internal memory or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 74 of the type well known in the art which charges a storage capacitor to a predetermined voltage level and a discharge circuit 76 for discharging the storage capacitor within circuit 74 by a predetermined amount to provide a controlled discharge output of electrical energy when required to the atria of the heart. To that end, the discharge circuit 76 is coupled to the first electrode 44 and the second electrode 46 of the second lead 36 for applying the cardioverting or defibrillating electrical energy to the atria. Lastly, the defibrillator 30 includes a depletable power source 78, such a lithium battery, for providing power to the electrical components of the atrial defibrillator 30.

The sense amplifier 52 and the R wave detector 54 continuously detect the occurrence of ventricular activations of the right ventricle 12. The occurrence of the detected ventricular activations are recorded in the event record stage 64. As disclosed in the aforementioned copending U.S. applications Ser. Nos. 07/685,130 and 07/856,514, herein incorporated by reference, when the time intervals between immediately successive R waves recorded in event recorder 64 indicate the probability of an episode of atrial fibrillation, the microprocessor 62 enables the atrial fibrillation detector 70, sense amplifier 50, and the analog to digital converter 60. As the sense amplifier 50 senses heart activity of the atria, the digital samples or data provided by the analog to digital converter 60 are recorded in the event recorder 64. Since the sense amplifier 50 senses only atrial activity as previously described, the digital samples recorded in the event recording stage 64 from the atrial channel to be processed by the atrial fibrillation detector will only represent atrial activity of the heart. The atrial fibrillation detector 70 processes the digital samples recorded in the event recorder stage 64 in accordance with any one of the aforementioned algorithms cited in the aforementioned referenced copending applications. If it determines that the atria 16 and 18 are in fibrillation and thus in need of cardioversion, the charge delivery control 72 cause the charger and storage capacitor circuit 74 to charge the storage capacitor within circuit 74. The charge delivery control 72 cause the discharge circuit 76 to discharge the capacitor of circuit 74 for applying cardioverting electrical energy to the atria 16 and 18 in synchronism with an R wave detected by sense amplifier 52 and R wave detector 54.

Figure 2:
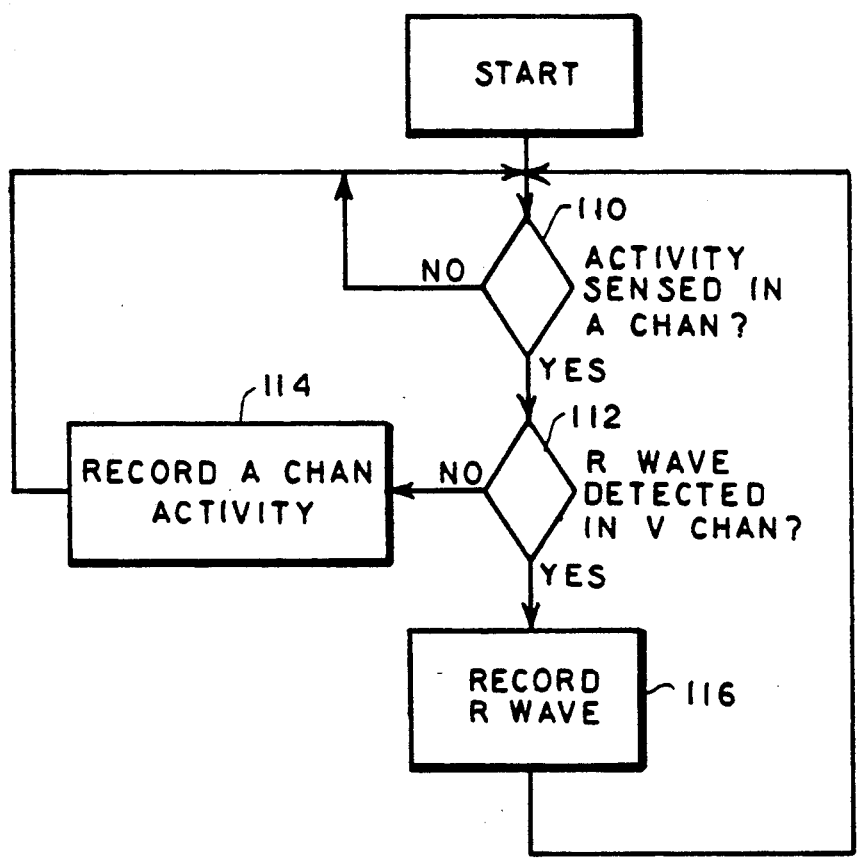
FIG. 2 is a flow diagram illustrating the manner in which the atrial defibrillator of FIG. 1 may be implemented in accordance with the present invention for reliably sensing and recording atrial activity of the heart.

To further assure that the atrial fibrillation detector 70 only processes digital samples representative of atrial activity of the heart when determining if atrial fibrillation is present, the microprocessor controls the recording of the atrial activity and the ventricular activations in accordance with the flow diagram of FIG. 2. The process of FIG. 2 is implemented when the atrial fibrillation detector 70, sense amplifier 50, and analog to digital converter 60 are enabled.

The selective recording process begins at step 110 wherein the microprocessor 62 determines if heart activity is being sensed by the atrial channel including lead 36 and sense amplifier 50. If the atrial channel is not sensing heart activity, the microprocessor returns. However, if the atrial channel is sensing heart activity, the microprocessor proceeds to step 112 to determine if the ventricular channel including lead 34, sense amplifier 52 and R wave detector 54 is detecting an R wave. If the ventricular channel is not detecting an R wave, the microprocessor then in step 114 records the digital samples or data of the heart activity sensed by the atrial channel in the event recording stage 64 and returns. However, if the ventricular channel is detecting an R wave, the microprocessor in step 116 records the detected R wave in the event recording stage before returning and the blanking stage 66 precludes the event recording stage 64 from recording the heart activity sensed by the atrial channel.

The foregoing selective recording process illustrated in FIG. 2 continues as described above as long as the atrial channel and the atrial fibrillation detector 70 are enabled. This selective recording process assures that the digital samples provided by the analog to digital converter 60 are only representative of atrial activity of the heart. As a result, the determination by the atrial fibrillation detector 70 as to whether the atria are in need of cardioversion is based solely upon atrial activity of the heart.

As will be appreciated by those skilled in the art, either the disabling of sense amplifier 50 or the selective recording process illustrated in FIG. 2 or both together may be utilized in practicing the present invention. Further, as previously described, the sense amplifier 50 may be disabled by either short circuiting its inputs 50a and 50b or by selecting the relatively low gain of amplifier 50 when an R wave is detected to preclude amplifier 50 from sensing an R wave of the heart. Any one of the foregoing alternatives or any combination thereof will assure that only atrial activity of the heart will be relied upon by the atrial fibrillation detector 70 for determining if the atria are in fibrillation and hence in need of cardioversion.

While particular embodiments of the present invention have been shown and described, modifications may be made. For example, if the atrial fibrillation detector 70 is implemented to process both sensed atrial activity and ventricular activations in real time rather than from stored data indicative of that activity or those events, the blanking stage 66 may be implemented to cause the atrial fibrillation detector to ignore the sensed atrial activity during detected ventricular activations. In this manner, the atrial fibrillation detector 70 would rely only on sensed atrial activity for detecting atrial fibrillation. Further, if the atrial fibrillation detector is implemented to process stored data of atrial activity and ventricular activations, the stored data may be time stamped. This would permit all atrial activity and ventricular activations to be recorded in the event recording stage 64 and the microprocessor 62 to process the data in a manner virtually identical to the manner illustrated in FIG. 2 wherein the microprocessor through blanking stage 66 may read the time stamps and cause the atrial fibrillation detector 70 to ignore all heart activity events recorded from the atrial channel during ventricular activations. In this further implementation, the atrial fibrillation detector 70 would rely on only atrial activity in detecting the presence of atrial fibrillation. It is therefore intended in the appended claims to cover all such changes and modifications which fall within the true spirit and scope of the invention.

What is claimed is:

1. An implantable atrial defibrillator for applying cardioverting electrical energy to the atria of a human heart in need of cardioversion, said atrial defibrillator comprising:
    first detecting means adapted for sensing activity of the heart in at least one of the atria of the heart;
    atrial fibrillation detecting means responsive to the activity of the heart sensed by said first detecting means for determining when the atria of the heart are in need of cardioversion;
    second detecting means for detecting ventricular activations of the heart;
    cardioverting means for applying cardioverting electrical energy to the atria of the heart when the atria of the heart are in need of cardioversion and being responsive to said second detecting means for applying said cardioverting electrical energy to the atria of the heart in predetermined time relation to a detected ventricular activation; and
    means for causing said atrial fibrillation detecting means to ignore, in determining when the atria are in need of cardioversion, the activity of the heart sensed by said first detecting means during the detection by said second detecting means of the ventricular activations of the heart.

2. An atrial defibrillator as defined in claim 1 further including event recording means for recording the sensed activity of the heart, wherein said atrial fibrillation detecting means is responsive to the activity of the heart recorded in said recording means for determining when the atria are in need of cardioversion, and wherein said means for causing precludes said event recording means from recording activity of the heart sensed by said first detecting means during the detection of the ventricular activations of the heart by said second detecting means.

3. An atrial defibrillator as defined in claim 2 wherein said event recording means further records ventricular activations of the heart detected by said second detecting means.

4. An atrial defibrillator as defined in claim 1 further including event recording means for recording the activity of the heart sensed by said first detecting means and detected by said second detecting means, wherein said atrial fibrillation detecting means is responsive to the recorded events in said recording means for determining when the atria are in need of cardioversion, and wherein said means for causing causes said atrial fibrillation detecting means, in determining when the atria are in need of cardioversion, to ignore the recorded activity of the heart sensed by said first detecting means during the detection of the ventricular activations of the heart by said second detecting means.

5. A method of applying cardioverting electrical energy to the atria of a human heart in need of cardioversion, said method comprising the steps of:
    sensing activity of the heart in at least one of the atria of the heart;
    detecting ventricular activations of the heart;
    providing an atrial fibrillation detector for determining from the activity of the heart sensed in the at least one of the atria when the atria are in need of cardioversion;
    causing said atrial fibrillation detector, in determining when the atria are in need of cardioversion, to ignore the activity of the heart sensed in the at least one of the atria during the detection of the ventricular activations of the heart; and
    applying cardioverting electrical energy to the atria of the heart when the atria are in need of cardioversion and in predetermined timed relation to be detected ventricular activation of the heart.

6. A method as defined in claim 5 wherein said sensing step includes recording the activity of the heart sensed in the at least one of the atria, wherein said causing step includes terminating said recording at the beginning of each detected ventricular activation and resuming said recording immediately after the completion of each detected ventricular activation, and wherein said atrial defibrillation detector determines when the atria are in need of cardioversion responsive to the recorded activity.

7. A method as defined in claim 5 wherein said sensing step includes recording the activity of the heart sensed in the at least one atria of the heart, wherein said detecting step includes recording the detected ventricular activations, and wherein said causing step includes causing said atrial fibrillation detector to ignore the recorded sensed activity of the heart recorded during the detection of ventricular activations in determining when the atria are in need of cardioversion.

8. A method of applying cardioverting electrical energy to the atria of a human heart in need of cardioversion, said method comprising the steps of:
    providing a first electrode and a second electrode;
    establishing electrical contact between said first electrode and a point within the coronary sinus or great cardiac vein of the heart;

establishing electrical contact between said second electrode and a point within the superior vena cava or right atrium of the heart;

sensing activity of the heart between said first and second electrodes;

detecting ventricular activations of the heart;

providing an atrial fibrillation detector for determining from the activity of the heart sensed between said first and second electrodes when the atria are in need of cardioversion;

causing said atrial fibrillation detector, in determining when the atria are in need of cardioversion, to ignore the activity of the heart sensed between said first and second electrodes during the detection of the ventricular activations; and applying cardioverting electrical energy to the atria of the heart when the atria are in need of cardioversion and in predetermined timed relation to a detected ventricular activation of the heart.

9. A method as defined in claim 8 wherein said applying step includes applying said cardioverting electrical energy to said first and second electrodes.

* * * * *